106-80
7/27/82    XR    4,341,559

United States Patent [19]
Friedemann et al.

[11] 4,341,559
[45] Jul. 27, 1982

[54] BINDERS BASED UPON SOLUTIONS OF ALKALI METAL SILICATES

[75] Inventors: Wolfgang Friedemann; Norbert Maak, both of Neuss; Kurt Feulner, Essen, all of Fed. Rep. of Germany

[73] Assignee: Henkel Kommanditgesellschaft auf Aktien, Düsseldorf-Holthausen, Fed. Rep. of Germany

[21] Appl. No.: 204,562

[22] Filed: Nov. 6, 1980

[30] Foreign Application Priority Data

Nov. 17, 1979 [DE] Fed. Rep. of Germany ....... 2946500

[51] Int. Cl.³ ................................................. B28B 7/34
[52] U.S. Cl. ............................ 106/38.35; 106/38.5 R; 106/80; 106/84; 106/162; 164/16
[58] Field of Search ........... 106/38.35, 80, 84, 38.5 R, 106/162; 164/16

[56] References Cited

U.S. PATENT DOCUMENTS

2,016,962 10/1935 Flint ..................................... 260/127
2,182,929 12/1939 Werntz ................................. 260/211
2,926,098 2/1960 Ilenda et al. ........................ 106/38.35
4,194,918 3/1980 George et al. ...................... 106/38.35

*Primary Examiner*—Lorenzo B. Hayes
*Attorney, Agent, or Firm*—Hammond & Littell, Weissenberger and Muserlian

[57] ABSTRACT

This invention is directed to binder compositions based upon aqueous solutions of alkali metal silicates. More particularly, this invention is directed to binder compositions consisting essentially of (a) aqueous alkali metal silicate solutions having a molar ratio of $SiO_2:Me_2O$ of from about 2.0:1 to 3.4:1, with Me signifying an alkali metal, and a solids content of from about 35 to 50 percent by weight, based on the weight of the total alkali metal solution, and (b) from about 0.1 to 10 percent by weight, based upon the weight of the total binder composition, of at least one reductively aminated mono-, di-, or oligosaccharide, and the use of such binder compositions in the preparation of molds or cores for metal casting.

10 Claims, No Drawings

BINDERS BASED UPON SOLUTIONS OF ALKALI METAL SILICATES

FIELD OF THE INVENTION

This invention is directed to binder compositions based upon aqueous solutions or alkali metal silicates comprising additional organic compounds. More particularly, this invention is directed to the use of such binder compositions in the manufacture of molds and cores for metal casting.

BACKGROUND OF THE INVENTION

Binder compositions based upon aqueous alkali metal silicate solutions have been known for a long time and are used on a large scale in manufacturing. The alkali metal silicate solutions, particularly sodium silicate solutions, usually have a molar ratio of $SiO_2:Me_2O$ (Me=alkali metal) in the range from about 2.0:1 to 3.4:1 as well as a solids content of from about 35 to 50 percent by weight. Binder compositions of this type are used, for example, in the preparation of mineral insulating materials, impregnating substances, coating materials, paints, and putties as well as in glues for the gluing of wood, paper, ceramics, and mineral materials.

Such binders can also be used for the preparation of molds for metal casting. For this purpose, the aqueous alkali metal silicate solution usually is mixed with fine fillers such as sand, and the resulting mixture is molded into the desired shape and hardened with the aid of hardeners. Suitable hardeners for this purpose include, for example, carbon dioxide gas, compounds with acid reaction, or acid-evolving compounds. A considerable disadvantage of this method is that it is extremely difficult to remove the finished forms, that is, the molds and cores, from the solidified castings after metal casting.

Various carbohydrates, such as sugar, molasses, starch, or starch or cellulose derivatives, usually are added to the binders to facilitate breaking of the molds after the completed casting. However, these additives, which may be contained in amounts of up to about 10 percent by weight in the binder composition, generally result in an undesirable absorption of water by the hardened molds during storage. This leads to a considerably reduced durability of the molds, particularly around their edges.

Consequently, there has been a need to develop a binder based upon aqueous alkali metal silicate solutions that is particularly suitable for the preparation of molds for metal casting without the disadvantages listed above.

OBJECTS OF THE INVENTION

It is an object of the invention to provide novel binder compositions.

It is also an object of the invention to provide novel binder compositions based upon aqueous solutions of alkali metal silicates and containing additional organic compounds.

It is a further object of the invention to provide a method of using such novel binder compositions in the manufacture of molds and cores for metal casting.

These and other objects of the invention will become more apparent in the discussion below.

DETAILED DESCRIPTION OF THE INVENTION

Applicants have surprisingly found binder compositions based upon alkali metal silicate solutions whereby the resulting molds have improved characteristics. According to the invention, the binder compositions are based upon aqueous solutions of alkali metal silicates wherein the molar ratio of $SiO_2:Me_2O$, Me representing an alkali metal, is in the range of from about 2.0:1 to 3.4:1, the solids content is from about 35 to 50 percent by weight, and the composition also comprises reductively aminated mono-, di-, or oligosaccharides.

It has been found that an addition of reductively aminated saccharides to the binder composition considerably improves the binder's characteristics for industrial application for the preparation of molds. This becomes apparent, on the one hand, in a strongly reduced hygroscopicity of the hardened molds and, on the other hand, in an easier breaking of the molds used for casting. Due to the lower hygroscopicity of the molds, their resistance to pressure, particularly in the area of the edges, remains intact for a longer time, even during storage at room temperature. Furthermore, it has been found that good initial resistance to pressure is obtained by hardening with carbon dioxide gas, even when the molds are hardened for short periods of time. The handling and transporting of the hardened molds as well as their removal from the finished casting, are facilitated considerably by this measure.

Reductively aminated mono-, di-, or oligosaccharides are reaction products of corresponding saccharides or saccharide mixtures with conventional amination components, which are formed under the action of hydrogen. Suitable amination components for such reaction products are ammonia and primary and secondary amines, as well as mixtures of such compounds. Specific examples of suitable amination components include methylamine, ethylamine, butylamine, ethanolamine, dimethylamine, diethylamine, diethanolamine, and ammonia. Among the saccharides that can form such reaction products are, in addition to the monosaccharides, all reducing di- and oligosaccharides, such as, for example, glucose, galactose, maltose, lactose, cellobiose, maltotriose, and maltodextrines as well as other oligomeric starch metabolites with a reducing effect, such as glucose syrup.

The reaction products according to the invention (aminosaccharides for short) are obtained, for example, by reaction of reducing saccharides with the amination component in an aqueous medium and in the presence of hydrogen and a conventional hydrogenation catalyst in a pressure vessel. One such method for the preparation of such products is described, for example, in U.S. Pat. No. 2,016,962, incorporated herein by reference. Separation of aminosaccharides formed is usually not necessary since these can be used, for example, in the form of a 30 percent by weight aqueous solution according to the invention.

The bases for the alkali metal silicate solutions to be used according to the invention are usually commercial water glass solutions with molar ratios and solids contents in the ranges given above. Corresponding aqueous alkali metal silicate solutions also may be obtained by dissolving powdered, soluble alkali metal water glass compounds. To provide good binding capacity, the binders according to the invention preferably contain an alkali metal silicate with a molar ratio of $SiO_2:Me_2O$ in the range from about 2.2:1 to 2.6:1, Me standing for sodium and/or potassium.

Thus, potassium water glass substances, sodium water glass substances, and corresponding mixed water glass substances, can be used for the binder compositions according to the invention.

Binders according to the invention usually contain from about 0.1 to 10 percent by weight, based on the weight of the total binder composition, of a reductively aminated mono-, di-, or oligosaccharide. The aminosaccharide generally is added to the binder composition in the form of an aqueous solution. Preferably the aminosaccharide is added in amounts of from about 0.5 to 5 percent by weight, based on the weight of the total binder composition, since sufficiently good industrial or technical applications are obtained with such amounts in the preparation of molds. Preferred, suitable reductively aminated mono-, di-, or oligosaccharides are reaction products of glucose, galactose, maltose, or their mixtures with methylamine, ethylamine, butylamine, ethanolamine, or mixtures thereof, obtained under the action of hydrogen.

With respect to a lower hygroscopicity of the molds, a small addition of potassium metaborate to the binder has also been found advantageous. Accordingly, the binders according to the invention may contain from about 0.1 to 2 percent by weight, based on the weight of the total binder composition, of $B_2O_3$ in the form of potassium metaborate. The potassium metaborate, which may be obtained, for example, by mixing boric acid with the stoichiometrically necessary amount of concentrated potassium hydroxide solution, is advantageously also added to the binder in the form of an aqueous solution.

As explained earlier, the binder compositions of the invention may be used to advantage in the preparation of molds of powdered fillers, particularly of molds and/or cores for metal casting. The preparation of such molds proceeds in a well-known manner: generally, from about 3 to 6 percent by weight of the binder composition according to the invention is mixed intensively with a powdered filler, usually arenaceous quartz, and hardened with the addition of a suitable hardener. Suitable hardeners include all inorganic and/or organic hardeners normally used for this purpose, such as, for example, carbon dioxide gas, esters of polyhydric alcohols such as diacetin or triacetin, succinates, glutarates, and adipates. The mold is produced by forming and then treated with carbon dioxide gas to harden, or the solid hardeners are added to the binder composition and the filler and binder composition is molded and allowed to harden.

In addition to the above, the binder compositions according to the invention also may be used for all those purposes for which binder compositions based on aqueous alkali metal silicate solutions are normally used.

The following examples are intended to illustrate the invention and are not to be construed as limiting the invention thereto.

EXAMPLES

EXAMPLE 1

The binder used had the following composition:
90 percent by weight of sodium water glass with a molar ratio of $SiO_2:Na_2O$ of 2.48:1 and a solids content of 47 percent by weight; and
10 percent by weight of a 30 percent by weight aqueous solution of methylglucamine (reaction product of methylamine with glucose under hydrogen).

The binder was obtained by mixing the aqueous solutions.

The binder was used for the preparation of molds in the following manner:

One hundred parts by weight of arenaceous quartz (granulation H34) were mixed intensively for two minutes with 4 parts by weight of the binder. Then, 170 gm of the mixture were formed into cylindrical cores with a height of 60 mm and a diameter of 50 mm and compressed in a compressor manufactured by Georg Fischer Aktiengesellschaft, Schaffhausen, Switzerland. The cores obtained were then hardened with carbon dioxide gas (5 seconds at 25° C. and 1.5 bar line pressure). Immediately after, the initial value of the resistance of pressure of the cores was determined with a compressive strength test device manufactured by Georg Fischer Aktiengesellschaft, Schaffhausen, Switzerland. The value obtained is set forth in the Table below.

Additional determinations of the resistance to pressure were carried out after 3 days of storage at room temperature and a relative humidity of 50 percent, as well as after the same storage time and subsequent annealing of the sample cores at 900° C. for two minutes. The values measured are also set forth in the Table. The hygroscopicity of the sample cores was determined in terms of the percent of water absorbed, based on the weight of the sample cores, after storage over distilled water for 8 days at room temperature in a desiccator (relative humidity, approximately 98 percent), and the resulting data is also set forth in the Table. The solidity of the edges of the test cores—initial value as well as after three days of storing at room temperature—was determined manually.

In the following examples binder compositions were prepared according to the procedure of Example 1, unless otherwise noted.

EXAMPLE 2

The binder used contained, in contrast to Example 1, 3 percent by weight of methylmaltamine (reaction product of methylamine with maltose under the action of hydrogen) as the aminosaccharide. The results obtained with this binder in the preparation of molds are set forth in the Table below.

EXAMPLE 3

The binder used contained, in contrast to Example 1, 3 percent by weight of n-butylglucamine (reaction product of n-butylamine with glucose under the action of hydrogen) as aminosaccharides. The results obtained with the binder prepared are set forth in the Table below.

EXAMPLE 4

The binder used contained, in contrast to Example 1, 3 percent by weight of a reaction product of glycose syrup with ethylamine and hydrogen as aminosaccharides. The results obtained with the binder are set forth in the Table below.

EXAMPLES 5 to 9

An amount of 1 percent by weight, based on the weight of the total binder composition, of $B_2O_3$, in the form of an aqueous potassium metaborate solution, was added to a binder composition analogous to that prepared in Example 1. The hardening time of the sample molds was varied in the preparation of the molds by treatment with carbon dioxide gas:
Example 5: gassing time 5 seconds.
Example 6: gassing time 4 seconds.
Example 7: gassing time 3 seconds.
Example 8: gassing time 2 seconds.
Example 9: gassing time 1 second.

The results obtained with the binders are set forth in the Table below.

EXAMPLE 10

The binder used contained, in contrast to Example 1, 0.1 percent by weight of methylgalactamine (reaction product of methylamine with galactose under the action of hydrogen) as the aminosaccharide. The results obtained with the binder are set forth in the Table below.

EXAMPLE 11

The binder used contained, in contrast to Example 1, 5 percent by weight of hydroxyethylglucamine (reaction product of ethanolamine with glucose under the action of hydrogen) as the aminosaccharide. The results obtained with the binder are set forth in the Table below.

EXAMPLE 12

The binder used contained, in contrast to Example 1, 10 percent by weight of ethylglucamine (reaction product of ethylamine with glucose under the action of hydrogen) as the aminosaccharide. The results obtained with the binder are set forth in the Table below.

EXAMPLE 13

The binder used contained, in contrast to Example 1, 3 percent by weight of a reaction product of maltodextrin with methylamine and hydrogen as aminosaccharide. The results obtained with the binder are set forth in the Table below.

EXAMPLE 14

The binder used contained, analogously to Example 1, methylglucamine as aminosaccharide, but in an amount of 0.5 percent by weight. The results obtained with the binder are set forth in the Table below.

EXAMPLE 15

The binder used has the following composition:
90 percent by weight of sodium water glass with a molar ratio of $SiO_2:Na_2O$ of 2.6:1 and a solids content of 41.5 percent by weight, and
10 percent of a 30 percent by weight aqueous solution of methylglucamine analogous to Example 1.

The results obtained are set forth in the Table below.

EXAMPLE 16

The binder used had the following composition:
90 percent by weight of a sodium-potassium mixed water glass solution with a total molar ratio for $SiO_2:Me_2O$ of 2.6:1, equal amounts of sodium and potassium water glass, and a solids content of 39.7 percent by weight, and
10 percent by weight of a 30 percent by weight aqueous solution of methylglucamine analogous to Example 1.

The results obtained are set forth in the Table below.

COMPARISON EXAMPLE A

The binder composition of this comparison example did not contain any aminosaccharide but contained instead hexite, a typical additive. The binder used had the following composition:
90 percent by weight of sodium water glass solution analogous to Example 1, and
10 percent by weight of a 70 percent by weight aqueous solution of hexite ($C_6H_8(OH)_6$).

Molds were prepared analogously to the procedure of Example 1. The results obtained are set forth in the Table below.

The results of testing molds prepared from the binder compositions of Examples 1 to 16 and Comparison Example A are set forth in the Table below. The indicated variables and symbols have the following meanings:
a = initial value
b = after 3 days of storing at room temperature
c = after 3 days of storing at room temperature and subsequent annealing (900° C., 2 minutes)
++ = solidity of the edges very good
+ = solidity of the edges good
(+) = solidity of the edges satisfactory
− = solidity of the edges poor

TABLE

| Example | Organic Substance Present in Binder (Percent by Weight) | Resistance to Pressure (bar) a | b | c | Hygroscopicity (Percent by Weight) | Solidity of Edges a | b |
| --- | --- | --- | --- | --- | --- | --- | --- |
| 1 | 3 | 5.4 | 70 | 4.1 | 0.93 | (+) | ++ |
| 2 | 3 | 8.4 | 66 | 3.5 | 0.87 | (+) | ++ |
| 3 | 3 | 7.8 | 67 | 5.3 | 1.29 | (+) | ++ |
| 4 | 3 | 5.1 | 69 | 8.5 | 1.42 | (+) | ++ |
| 5 | 3 | 6.2 | 30 | 7.0 | 0.87 | (+) | + |
| 6 | 3 | 11.0 | 58 | 4.6 | 1.34 | (+) | ++ |
| 7 | 3 | 9.1 | 64 | 4.3 | 1.39 | (+) | ++ |
| 8 | 3 | 6.3 | 56 | 5.5 | 1.37 | (+) | ++ |
| 9 | 3 | 9.2 | 46 | 5.7 | 1.33 | (+) | ++ |
| 10 | 0.1 | 3.8 | 84 | 8.8 | 1.20 | (+) | ++ |
| 11 | 5 | 5.9 | 50 | 9.0 | 1.31 | (+) | ++ |
| 12 | 10 | 9.9 | 32 | 3.8 | 1.29 | (+) | + |
| 13 | 3 | 6.5 | 61 | 8.8 | 1.32 | (+) | ++ |
| 14 | 0.5 | 4.0 | 76 | 5.8 | 0.95 | − | (+) |
| 15 | 3 | 7.0 | 58 | 4.8 | 0.78 | (+) | + |
| 16 | 3 | 9.4 | 42 | 3.4 | 0.67 | (+) | + |
| A | 7 | 5.6 | 44 | 18.0 | 1.76 | (+) | + |

The values compiled in the Table show that, in comparison with the Comparison Example A, the hygroscopicity of the prepared test molds can be reduced considerably and the resistance of the test molds to pressure during storage can be increased considerably, by the use of the binder compositions according to the invention. Furthermore, a crucial advantage is the improved breaking behavior after heating of the test molds prepared from binder compositions according to the invention. The resistance to pressure data, determined after annealing, are 25 to 50 percent of the value for the comparison example. The advantages obtainable with the binders according to the invention can be achieved with considerably lower concentrations of organic substance in the binder. An addition of potassium metaborate to the binder also results in improved properties of the test molds at shorter gassing time.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A binder composition consisting essentially of (a) a concentrated aqueous solution of an alkali metal silicate solution having a molar ratio of $SiO_2:Me_2O$ of from about 2.0:1 to 3.4:1, with Me signifying an alkali metal, and a solids content of from about 35 to 50 percent by weight, based upon the weight of the total alkali metal solution, and (b) from about 0.1 to 10 percent by weight, based on the weight of the total binder composition, of at least one reductively animated monosaccharide, disaccharide, or oligosaccharide selected from the group consisting of reaction products of a monosaccharide or reducing disaccharide or oligosaccharide with ammonia, a primary amine, or a secondary amine and formed under the action of hydrogen.

2. A binder composition of claim 1, wherein the molar ratio of $SiO_2:Me_2O$ is from about 2.2:1 to 2.6:1 and Me represents sodium, potassium, or both.

3. A binder composition of claim 1 which contains from about 0.5 to 5 percent by weight, based on the weight of the total binder composition, of the reductively aminated mono-, di-, or oligosaccharide.

4. A binder composition of claim 1, wherein the reductively aminated mono-, di-, or oligosaccharide comprises a reaction product of glucose, galactose, maltose, or a mixture thereof with methylamine, ethylamine, butylamine, or ethanolamine, or a mixture thereof and formed under the action of hydrogen.

5. The binder composition of claim 1 which also contains from about 0.1 to 2 percent by weight, based on the weight of the total binder composition, of potassium metaborate.

6. A method of preparing a mold or core which comprises admixing binder composition of claim 1 with arenaceous quartz and hardening the admixture with at least one inorganic or organic hardener.

7. The method of claim 6, wherein the mold or core is employed for metal casting.

8. The method of claim 6, wherein the admixture of binder composition and quartz is formed into a shape and then treated with carbon dioxide.

9. A method of preparing a mold or core which comprises admixing binder composition of claim 1 with arenaceous quartz and hardening the admixture with a hardener selected from the group consisting of carbon dioxide gas, diacetin, and triacetin.

10. A mold or core prepared according to the method of claim 6.

* * * * *